United States Patent [19]

Kuhn et al.

[11] Patent Number: 5,783,725
[45] Date of Patent: Jul. 21, 1998

[54] STABILIZED LACTIC ACID MENTHYL ESTER

[75] Inventors: Walter Kuhn; Alfred Körber, both of Holzminden; Roland Langner, Bevern; Detlef Hagena, Stahle, all of Germany

[73] Assignee: Haarmann & Reimer GmbH, Holzminden, Germany

[21] Appl. No.: 799,856

[22] Filed: Feb. 13, 1997

[30] Foreign Application Priority Data

Feb. 27, 1996 [DE] Germany ............... 196 07 278.6

[51] Int. Cl.⁶ ................................................ C07C 67/62
[52] U.S. Cl. .................................................. 560/188
[58] Field of Search .................................... 560/188

[56] References Cited

U.S. PATENT DOCUMENTS 3,449,407  6/1969  Theimer et al. .................. 560/188
3,835,169  9/1974  Kraft et al. ........................ 560/188
5,602,178  2/1997  Caroselli et al. .................. 514/529

FOREIGN PATENT DOCUMENTS 2608226  9/1977  Germany ......................... 560/188

OTHER PUBLICATIONS

Houben–Weyl, vol. VIII, p. 517.

*Primary Examiner*—James H. Reamer
*Attorney, Agent, or Firm*—Sprung Kramer Schaefer & Briscoe

[57] ABSTRACT

Lactic acid menthyl ester can be stabilized by addition of alkali metal carbonate and/or bicarbonate and/or alkaline earth metal carbonate and/or bicarbonate.

1 Claim, No Drawings

STABILIZED LACTIC ACID MENTHYL ESTER

Lactic acid menthyl ester (in the following: LME)

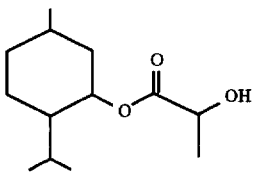
(I)

is a compound having a physiological cooling action on the skin and mucosa of the body which can be employed in consumer products with which a long-lasting physiological cooling action is desired: for example in semi-luxury consumable goods such as chewing gum, chewing tobacco, cigarettes, ice-cream, confectionery and drinks, and in pharmaceutical preparations, body care compositions or cosmetic preparations such as tooth cleansing compositions, mouthwashes, perfumes, powders, lotions, ointments, oils, creams, shaving lotions and shampoos.

LME is usually prepared by acid-catalyzed esterification of commercially available L-lactic acid with L-menthol.

Suitable esterification catalysts are described, for example, in Methoden der Organischen Chemie [Methods of Organic Chemistry] (Houben-Weyl), Volume VIII, page 517, Georg Thieme Verlag, Stuttgart 1952. Preferred catalysts include inorganic acids, such as sulfric acid, phosphoric acid and acid earths, organic acids, such as methanesulfonic acid and p-toluenesulfonic acid, and acid ion exchangers. The recommended amounts are 0.0001–0.1 mol, preferably 0.01–0.05 mol of catalyst per mole of lactic acid. Neutralization and washing of the reaction mixture are usually followed by purification by means of distillation, which gives the LME in a purity suitable for most uses (97 to 98%). In addition to LME, the distillate comprises D-lactic acid L-menthyl ester (1–2% and L-menthol (about 1%). During storage over several weeks, the product develops a pungent smell which renders it unusable for most intended uses. The reasons for this change in the product are not known.

Surprisingly, it has now been found that this undesirable change in the product does not occur in the presence of alkali metal carbonate and/or bicarbonate and/or alkaline earth metal carbonate and/or bicarbonate.

The invention thus relates to a mixture of

A. L-Lactic acid L-menthyl ester and, per part by weight of A,

B. 0.0001 to 0.05 part by weight of alkali metal carbonate and/or bicarbonate and/or alkaline earth metal carbonate and/or bicarbonate.

The mixtures according to the invention are stable to storage for several months; no changes in smell during storage are to be found.

The mixtures according to the invention can be prepared by any conceivable method, such as, for example, by dry mixing of the two components (preferably in powder form) or by dissolving the components in a solvent suitable for both constituents, such as aqueous methanol or aqueous acetone, and stripping off the solvent.

According to a preferred embodiment, the LME is recrystallized in the presence of the additive B, preferably after prior distillation, where the solvent used for the LME does not also simultaneously need to be a solvent for B; in other words: for the purpose of the invention, it is not necessary for the additive B to dissolve in dissolved LME; the additive B can be dispersed in the dissolved LME—preferably, of course, in finely divided form—and then separated off together with the LME crystals.

A preferred solvent for LME is acetone, the weight ratio of solvent/LME for the crystallization preferably being 0.5 to 10, preferably 1 to 3.

Sodium carbonate and bicarbonate and potassium carbonate and bicarbonate or calcium carbonate are preferably possible as the additive B.

The mixtures according to the invention can be employed for most purposes without additive B being removed beforehand.

The percentage data of the following Example in each case relate to the weight; parts are parts by weight.

EXAMPLE 1000 parts of distilled LME, comprising, according to the gas chromatogram, 97.3% of L-lactic acid L-menthyl ester, 1.4% of D-lactic acid L-menthyl ester and 0.8% of L-menthol were dissolved in 500 parts of acetone, to which 1 part of sodium bicarbonate had been added, at 40° C. The mixture is cooled in an ice-bath; seed crystals are added at 12° C. The mixture is then cooled to 5° C. in the course of 2 hours (while stirring). The crystal slurry is filtered off and dried in air.

According to the gas chromatograin, the resulting product comprises 99.7% of L-lactic acid L-menthyl ester. It can be stored for months without its sensorial properties changing.

We claim:

1. Mixture of

L-Lactic acid L-menthyl ester and, per part by weight of A, 0.0001 to 0.05 part by weight of alkali metal carbonate and/or bicarbonate and/or alkaline earth metal carbonate and/or bicarbonate.

* * * * *

UNITED STATES PATENT AND TRADEMARK OFFICE
CERTIFICATE OF CORRECTION

PATENT NO. : 5,783,725
DATED : July 21, 1998
INVENTOR(S) : Walter Kuhn et al

It is certified that error appears in the above-identified patent and that said Letters Patent is hereby corrected as shown below:

Column 2, Claim 1, Line 2      Before "L-Lactic acid" insert --A.--
Column 2, Claim 1, Line 4      Before "0.0001" insert --B.--

Signed and Sealed this

Seventh Day of September, 1999

Attest:

Q. TODD DICKINSON

Attesting Officer      Acting Commissioner of Patents and Trademarks